United States Patent [19]

Evenstad et al.

[11] Patent Number: 5,462,740
[45] Date of Patent: Oct. 31, 1995

[54] RECTALLY-ADMINISTERED, EPILEPTIC-SEIZURE-INHIBITING COMPOSITION

[75] Inventors: Kenneth L. Evenstad; Victoria A. O'Neill, both of Wayzata; Thomas R. Gorham, Brooklyn Park, all of Minn.

[73] Assignee: Athena Neurosciences, Inc., San Francisco, Calif.

[21] Appl. No.: 122,685

[22] Filed: Sep. 17, 1993

[51] Int. Cl.$^6$ ............................... A61F 9/02; A61K 47/38
[52] U.S. Cl. ................... 424/436; 424/DIG. 15; 514/774; 514/781; 514/785; 514/964
[58] Field of Search ............... 424/436, DIG. 15; 514/774, 781, 785, 964

[56] References Cited

U.S. PATENT DOCUMENTS

| | | | |
|---|---|---|---|
| 3,244,173 | 4/1966 | Berg | 604/192 |
| 3,958,011 | 5/1976 | Pigerol et al. | 424/320 |
| 3,968,230 | 7/1976 | Wright et al. | 424/274 |
| 3,988,472 | 10/1976 | Pigerol et al. | 424/320 |
| 4,126,672 | 11/1978 | Sheth et al. | 424/22 |
| 4,260,755 | 4/1981 | Moran et al. | 544/236 |
| 4,322,440 | 3/1982 | Fish et al. | 424/319 |
| 4,339,447 | 7/1982 | Boguth et al. | 424/244 |
| 4,411,894 | 10/1983 | Schrank et al. | 424/199 |
| 4,421,745 | 12/1983 | Inanaga et al. | 424/177 |
| 4,758,234 | 7/1988 | Orentreich et al. | 604/232 |
| 4,820,278 | 4/1989 | Balisky | 604/218 |
| 5,095,015 | 3/1992 | Albaugh | 514/214 |
| 5,112,856 | 5/1992 | Gaginella et al. | 514/456 |
| 5,122,598 | 6/1992 | Della Valle et al. | 536/20 |
| 5,130,430 | 7/1992 | Shaw | 544/346 |
| 5,143,731 | 9/1992 | Viegas et al. | 424/486 |
| 5,185,408 | 2/1993 | Tang et al. | 525/415 |
| 5,195,526 | 3/1993 | Michelson | 128/654 |
| 5,338,312 | 8/1994 | Montgomery | 604/230 |

OTHER PUBLICATIONS

*Remington's Pharmaceutical Sciences*, Mack Publishing Co., Ch. 56, pp. 1057–1066 and pp. 1072–1081, 18th ed., 1990.

*The Medical Letter*, vol. 31, Issue 783, 1–4, 1989.

Local Discomfort and Thrombophlebitis Following Intravenous Injection of Diazepam, A Comparison Between a Glycoferol–Water Solution and a Lipid Emulsion, D. Selander et al., *Acta Anaesth. Scand.*, 25, 516–518 (1981).

*The Lancet*, Mar. 2, 1985, pp. 518–519.

The Anticonvulsive Activity and Toxicity of Diazepam in Three Different Formulations. An Experimental Study in Mice, S. Hogskilde et al., *Acta Anaesthesiol Scand* 1987:31 pp. 289–291.

A Preliminary Investigation into the Formulation and Dissolution of Diazepam Suppositories, Susan Hughes et al, *Aust. J. Hosp. Pharm.* vol. 14, No. 2, 1984.

Diazepam Adsorption to Infusion Sets and Plastic Syringes, M. Winsnes, R. Jeppsson and B. Sjoberg, *Acta Anaesth. Scand.* 1981, 25, pp. 93–96.

A Double–Blind Comparative Study of Three Formulations of Diazepam in Volunteers, P. Forrest and D. C. Galletly, *Anaesth Intens Care* (1988), 16, pp. 158–163.

Primary Examiner—Carlos A. Azpuru
Attorney, Agent, or Firm—Merchant, Gould, Smith, Edell, Welter & Schmidt

[57] ABSTRACT

This invention provides a rectally administered composition for inhibiting epileptic seizure and to its methods of use. The composition contains, in a suitable solvent, an anti-epileptic agent for inhibiting epileptic seizure, a buffer for maintaining pH, and a thickener for imparting a viscosity to the composition effective for rectal administration by injection to a patient in epileptic seizure.

8 Claims, 2 Drawing Sheets

RECTALLY-ADMINISTERED, EPILEPTIC-SEIZURE-INHIBITING COMPOSITION

FIELD OF THE INVENTION

This invention relates to rectally administered compositions for inhibiting epileptic seizure and to their methods of preparation and application.

BACKGROUND OF THE INVENTION

Epilepsy is a paroxysmal, self-sustaining and self-limiting cerebral dysrhythmia characterized by an abnormal and excessive EEG (electroencephalograph) discharge and by a disturbance of consciousness. During an episode of epileptic seizure, there may be involuntary body movement or hyperactivity of the autonomic nervous system. Different kinds of epileptic seizures can display various clinical phenomena and EEG activities. Such variations in clinical phenomena and EEG activities form the basis of the characterization of seizures.

In tonic-clonic seizures (grand mal), a seizure is characterized by a sequence of tonic spasms of body musculature followed by clonic jerking movement. Tonic spasm is characterized by continuous tension whereas clonic movement refers to alternate muscular contraction and relaxation in rapid succession. In status epilepticus, a succession of grand mal seizures take place without intervening return of consciousness to the individual. See *Remington's Pharmaceutical Sciences*, Mack Publishing Co., Ch. 56, pp. 1057–1066 and pp. 1072–1081, 18th ed., 1990, which is incorporated by reference.

Generally, it is desirable to prevent epileptic seizures in humans by maintaining effective drug therapy. However, if seizure takes place, particularly for seizures with extensive tonic-clonic duration, such as status epilepticus, it may be necessary to give prompt treatment to inhibit or moderate the seizure in order to prevent injury to the patient, such as bruises, cuts, broken arms or even damage caused by anoxia. Anti-epileptic drugs (i.e., drugs that inhibit epileptic seizure, either before or after the onset of epileptic seizure) can be given intravenously for acute inhibition of the epileptic seizure. See "Drugs for Epilepsy", *The Medical Letter*, Vol. 31, Issue 783, 1–4, 1989. However, in situations in which there is involuntarily convulsive movement, intravenous administration of drugs is not desirable because the patient's uncontrolled movement may hinder injection or even cause injuries. Moreover, intravenous injection of diazepam, a preferred anti-epileptic drug, is sometimes painful and can cause thrombophlebitis, an inflammation of a vein associated with thrombus formation. See Selander et al., *Acta Anaesth. Scand.*, 25, 516–518 (1981).

A number of drugs are useful as anti-epileptic agents. See *Remington's Pharmaceutical Sciences*, supra. A convenient way to administer an anti-epileptic drug such as benzodiazepine, e.g. diazepam, is by ingestion so that the drug can be absorbed by the gastro-intestinal tract. Sheth et al. (U.S. Pat. No. 4,126,672) describe a sustained-release capsule for oral administration of diazepam. The capsules contain medicaments in combination with a hydrocolloid. Upon contact with gastric fluid, the hydrocolloid hydrates, forming an outside barrier which substantially retains the shape of the capsule. The hydrated layer slowly dissolves, releasing the medicament.

Fish et al. (U.S. Pat. No. 4,322,440) describe anti-convulsive compositions and methods of administering such compositions. The compositions are described as capable of being administered orally, as well as parenterally, i.e. via subcutaneous, intramuscular and intravenous injection. Fish et al. also disclose that the anti-convulsive compositions may be administered in the form of a rectal suppository. The suppository may be prepared by incorporating an active anti-convulsive agent into a shapable base material. Suitable suppository bases are described to include cocoa butter, glycerinated gelatin, hydrogenated vegetable oils, mixtures of polyethylene glucose, and fatty acid esters of polyethylene glycol.

However, for a patient having jerking movement because of seizure, the above-mentioned routes of drug administration are not practical. Intravenous injection of anti-epileptic agents is difficult. Oral administration is also impractical if the patient has no voluntary control of skeletal muscles. Rectal suppositories are slow-acting and therefore not effective for rendering fast relief of seizure. Therefore, there is a need for an epileptic-seizure-inhibiting composition that can be administered and absorbed quickly and safely.

SUMMARY OF THE INVENTION

The present invention provides a viscous, aqueous-based, epileptic-seizure-inhibiting composition effective to inhibit epileptic seizure. The composition is suitable for rectal administration by injection with a syringe-like applicator. The present invention is also directed to syringe assemblies and cartridges containing the composition and methods of using the assemblies and cartridges for delivery of the present composition. The epileptic-seizure-inhibiting composition is preferably a thickened solution that contains these ingredients: solvent, an anti-epileptic agent for inhibiting epileptic seizure, a pH adjusting agent such as a buffer system for maintaining a pH suitable for rectal administration, and a thickener for imparting a viscosity to the composition effective for rectal administration by injection to a patient in or threatened by epileptic seizure.

DETAILED DESCRIPTION OF THE INVENTION

Figure 1:
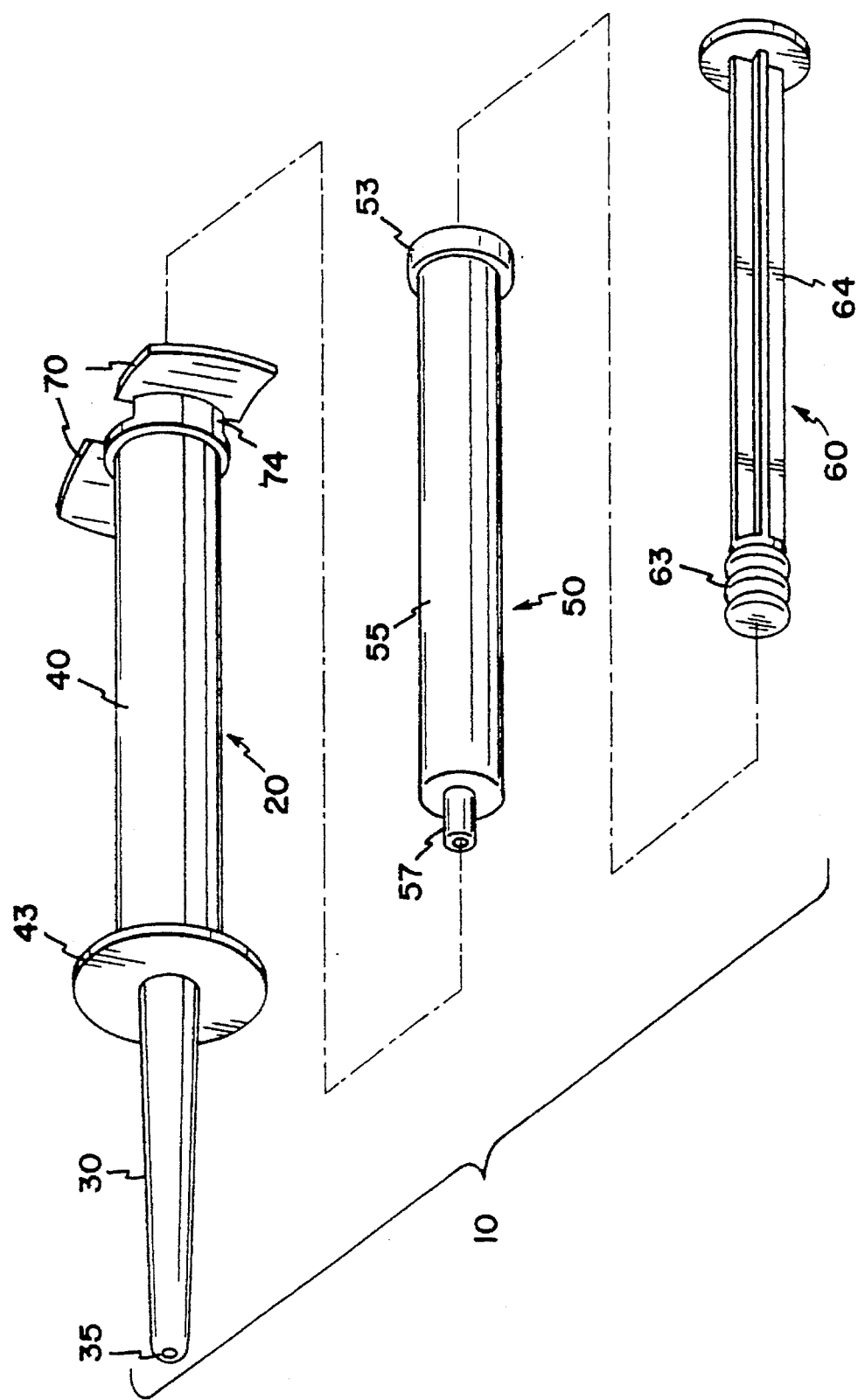
FIG. 1 is an exploded perspective view of an applicator for rectal administration of the seizure-inhibiting composition of the present invention.

One embodiment of the present invention is a composition for inhibiting epileptic seizures in a patient, such as status epilepticus seizures, acute cluster epilepsy seizures, acute repictcue seizures and febrile seizures. The composition is preferably a viscous solution or suspension, which is suitable for rectal insertion using a syringe-like applicator, yet is capable of being retained inside the patient's rectum without substantial leakage or drainage therefrom. The composition is useful for inhibiting or moderating an epileptic seizure in a patient during seizure. However, it can also be used to prevent the onset of seizure.

A. Anti-Epileptic Agent

A wide variety of anti-epileptic agents are known in the art. Many may be utilized in the epileptic-seizure-inhibiting composition of this invention. Representative examples of effective anti-epileptic agents include ethynyl amines such as deprenyl, eldeprine and eidepryl barbiturates such as mephobarbital, febarbamate, primidone, and phenobarbital sodium, benzodiazepines such as carbamezepine, lorazepam, and diazepam, hydantoins such as phenytoin sodium, mephenytoin and ethotoin BP, oxazolidinediones such as paramethadione and trimethadione, succinimides such as phensuximide and methsuximide, and dipropylacetic acid derivatives such as valproic acid, vaproate sodium and divalproex sodium. See *Remington's Pharmaceutical Sciences*, supra.

All anti-epileptic agents are not equally effective to inhibit all epilepsies because there are many different types of epilepsies, each having different etiology. Therefore, in the practice of the present invention, it is desirable to individualize their use in the drug therapy based on the particular seizure type and patient response. It is known that, for example, for grand mal seizures, and simple and partial complex seizures, drugs such as phenytoin, carbamazepine or valproate are more effective. For petit mal seizures, valproate is more effective.

When a patient is in epileptic seizure, in order to minimize injury to the patient due to tonic spasm and clonic movement, prompt administration of medication is required to inhibit the seizure. For seizures involving tonic spasm and clonic movement, particularly grand mal and status epilepticus seizures, even though many anti-epileptic agents, such as phenobarbital, can be used in the invention, the drug of choice is a benzodiazepine, particularly diazepam. Because of their relaxing effect in skeletal muscles, benzodiazepines, particularly diazepam, are also useful in the present invention for treating various types of epilepsies involving skeletal muscle contraction or spasm.

In treating epilepsy, occasionally, it may be preferable to use two or more anti-epileptic agents in the composition of the present invention. When two or more anti-epileptic agents are present in an epileptic-seizure-inhibiting composition, it is important to ensure that there is no deleterious interaction between the anti-epileptic agents so as not to reduce the effectiveness of the anti-epileptic agents or cause toxicity to the patient. Routine and standard procedures known in the art can be used to determine such interactions.

Typically, the total amount of anti-epileptic agent or agents present in the composition is about 0.1–2.5 wt-% of the total composition, preferably about 0.25–1.5 wt-% to about 7.5 wt-%. In the preferred embodiment in which diazepam is the only anti-epileptic agent in the composition, the concentration of diazepam is typically about 0.25–0.75 wt-% of the composition.

Preferably, a dose of epileptic-seizure-inhibiting composition is selected so that the effective amount of the anti-epileptic agent is in a suitable volume for a particular patient. Thus, a single dose of a composition of the present invention contains an amount of an anti-epileptic agent which is therapeutically effective to inhibit an epileptic seizure. This amount will depend on the particular anti-epileptic agent used. For commercially available anti-epileptic agents, information on the therapeutically effective amount for inhibiting epileptic seizure is available to the public.

Typically, the present composition can be administered so that single doses of diazepam of about 7.5 mg to 20 mg are delivered to an adult, so as to achieve a dose in the range of 0.2–0.5 mg/kg, and about 2 mg to 20 mg are delivered to a child, so as to achieve a dose of about 0.3 to 1.0 mg/kg. The amount can vary depending on the size and physical condition of the individual. The volume of the present epileptic-seizure-inhibiting composition to be administered also will vary with different patients. As a general guideline for using the composition of the present invention, e.g., wherein 0.5 wt-% diazepam is the anti-epileptic agent, typically the dosage is about 1.5 ml to about 5 ml for an adult (>12 years), preferably about 2–4 ml; and about 0.5 ml to about 4.0 ml for a child (under 12 years), preferably about 1.0 to 3.0 ml.

B. Thickener

The epileptic-seizure-inhibiting composition of the present invention contains an amount of a thickener effective for rendering the consistency of the composition effective for rectal administration to a patient in epileptic seizure by injection. To be effective as an injectable, rectally administered epileptic-seizure-inhibiting composition, the present composition preferably has a viscosity such that it can be quickly administered by injection, yet once administered, does not tend to leak out of or drain from the anus. If the viscosity of the composition is too low, because of the fluid consistency of the composition and movement of the patient, the composition may leak out of the rectum after administration. Such a leakage would make it difficult to produce the seizure-inhibiting effect desired. On the other hand, if the viscosity of the composition is too high, there may be difficulty in administering the composition into the rectum of a patient by injection.

Figure 2:
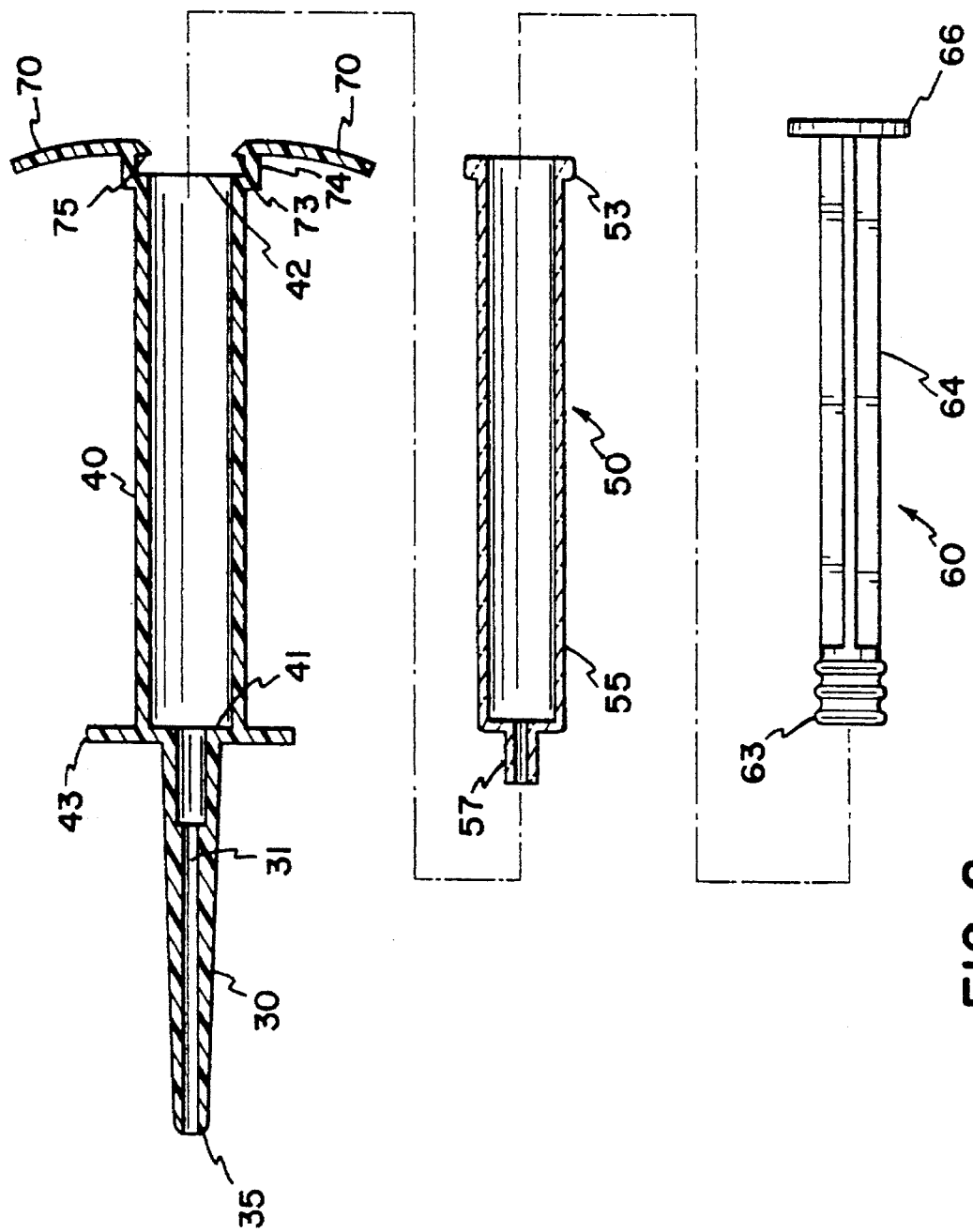
FIG. 2 is a cross-sectional view of the applicator of FIG. 1.

The viscosity generally will be low enough such that it will flow through, for example, a syringe-type applicator with a 6 cm long elongated, hollow member of about 2 mm internal diameter in less than about 5 seconds under moderate finger pressure. An example of such an applicator is shown in FIG. 1 and FIG. 2, which will be described hereinbelow. When administered into the rectum of a patient, the composition will remain substantially inside the rectum without substantially leaking out, and spread over the rectal mucosa without clumping. Generally, the leakage is less than 20% over 4 hours.

The composition typically has an apparent viscosity of about 1,000 to about 8,000 centipoise (cps), and more preferably, about 2,000 to about 6,000 cps, as measured using a Brookfield viscometer DV-IILV, spindle #3 at 12 rpm, sample size 150 ml at 21° C.

The desired viscosity of the composition may be maintained using a physiologically-acceptable thickener. Representative examples of thickeners that can be used include cellulose ethers such as methylcellulose, carboxy-methylcellulose, e.g., CMC-MV from Amend Drug and Chemical Co.; hydroxypropylcellulose, e.g., KLUCEL LF, GF, and MF from Aqualon; hydroxypropylmethylcellulose, e.g., METHOCEL E4MP, K100LVP, and E50LVP from Dow Chemical Co.; biogums, e.g., xanthan gum RHODIGEL from R. T. Vanderbilt Co.; carboxy vinyl polymers, e.g., Carbopol 934P from B. F. Goodrich Co.; and like. Preferred thickeners include hydroxypropylmethylcelluloses and hydroxypropylcelluloses with hydroxypropyl methylcellulose (molecular weight of about 22,000) being the most preferred.

Generally, an effective amount of a suitable thickener or thickeners is used to provide a viscosity within the desired range. The amount of a particular thickener used in the epileptic-seizure-inhibiting composition is dependent on the particular thickener used. Typically, the concentration of a suitable thickener such as a cellulose ether is about 1–10 wt-% of the composition, preferably about 2.5 to 7.5 wt-%.

For embodiments containing other anti-epileptic agents, based on the above-described viscosity and thickener information, the effective amount of a thickener selected may be determined by routine experimentation using the above-mentioned thickeners and an aqueous solution of a selected anti-epileptic agent, buffer system, and solubilizing agent if needed.

C. pH Adjusting Agent

The natural pH in the rectum is about 7.0. The optimal pH for stability for some anti-epileptic agents is slightly lower than 7. For example, for diazepam stability, the optimal pH is about 5.5. It is preferred that the pH of the present composition be adjusted to a value that is acceptable for rectal administration and stability of the anti-epileptic agent. Therefore, typically, the pH of the present composition containing diazepam will be neutral or mildly acidic, e.g., about 5.5 to 7.5. Preferably, the pH is about 6.2 to 7.2.

The pH of the rectally administered composition of the present invention can be maintained by a pH-adjusting agent, e.g., by a buffer system. A typical buffer system used in the invention contains organic acids and their corresponding sodium or potassium salts, with sodium salts being preferred. Examples of effective buffering systems are citric acids-sodium citrate, acetic acid-sodium acetate, benzoic acid-sodium benzoate, the preferred being benzoic acid-sodium benzoate. As with solubilizers, pH adjusting agents compatible with particular anti-epileptic agents are known in the art and often an anti-epileptic agent supplied in solution form contains suitable pH adjusting agents. One can vary the pH of the epileptic-seizure-inhibiting composition by fine-tuning the amount of the pH adjusting agents. For the preferred embodiment with diazepam as the anti-epileptic agent, the concentration of benzoic acid can be about 0.01 to 10 wt-% of the composition and the concentration of sodium benzoate can be about 1 to 10 wt-% of the composition to maintain the pH at about 5.5 to about 7.5.

D. Solvent

As used herein, the term "solvent" encompasses water, one or more organic co-solvents or mixtures thereof.

(i). Water

Water acts as a carrier for the different ingredients in the composition of the present invention. Generally, any commonly available source of water can be used. Preferably, the water is deionized water or distilled water, which has very little "hardness" ions that can lead to precipitation in the composition.

Typically, water can constitute about 25 to 95 wt-% of the composition, most preferably, about 25 to 50 wt-% of the composition. With the selected thickeners in the above-described concentration ranges, the present composition typically has a flowable viscous consistency.

(ii). Organic Solvent

In order for the anti-epileptic agent to be absorbed by the rectum, and for aesthetic reasons, the anti-epileptic agent preferably is maintained in solution in the present composition. Because some of the anti-epileptic agents may not be readily soluble in water, the water can be combined with one or more nontoxic, water-miscible organic solvents which solubilize the anti-epileptic agents and inhibit the precipitation thereof. Depending on the particular anti-epileptic agent, different organic solvents may be used. In the preferred case, wherein diazepam is the anti-epileptic agent, 1–2 nontoxic polyols or alkanols such as, propylene glycol and/or ethyl alcohol may be used as the organic solvent.

To facilitate the absorption of the anti-epileptic agent by the rectum, an organic solvent that can act as a physiologically-acceptable liquid surfactant can be selected to be included in the epileptic-seizure-inhibiting composition. An effective surfactant can modify the surface tension of the composition of the invention and facilitate coating of the epithelial cells in the rectum by the composition. Polyols such as propylene glycol and glycerol can act as surfactants or plasticizers in the composition.

Generally, the organic solvent or solvents are used in amounts effective to solubilize the anti-epileptic agent and to inhibit precipitation thereof in the epileptic-seizure-inhibiting composition, e.g., about 25 to 75 wt-% of a polyol or polyol-alkanol mixture may be employed. In the preferred embodiment in which the epileptic-seizure-inhibiting composition contains diazepam as the anti-epileptic agent, typically, propylene glycol is present at a concentration of about 25 wt-% to about 60 wt-% of the composition, and ethyl alcohol is present at a concentration of about 5 wt-% to about 15 wt-%. In some cases, the solvent used in the present composition can consist entirely of one or more nontoxic organic solvents.

E. Optional Ingredients

A physiologically-acceptable preservative can be optionally included in the epileptic-seizure-inhibiting composition to extend the shelf-life of the composition against bacterial attack. Benzyl alcohol is the preferred preservative, although other preservatives, for example, thimerosal, chlorobutanol, methyl parabens, propyl parabens and benzalkonium chloride may also be used. The concentration of the preservative needed in a composition varies with the preservative selected. Typically, a preservative is present in the epileptic-seizure-inhibiting composition at a concentration of about 0.01 wt-% to about 2.5 wt-% of the composition. For benzyl alcohol, the preferred concentration is about 1 wt-% to about 2.0 wt-%.

Ingredients of the composition of the present invention are preferably selected to avoid substances that can have a chemical reaction with the active anti-epileptic agent in the composition. The selection of ingredients and the proper concentration of such ingredients to avoid chemical reaction can be accomplished based on the present invention and by following standard and routine procedures, and reference to standard pharmacological texts and publications.

Another aspect of the selection of ingredients for such a composition can be to improve the aesthetic appeal of the composition. Generally, it is preferred that the composition be relatively clear. Therefore, the selection of the ingredients, their concentrations, and the pH of the composition is preferably done in a manner consistent with maintaining the composition precipitation-free.

F. Preparation of the Epileptic-seizure-inhibiting Composition

The composition of the invention can be prepared by mixing the ingredients according to generally accepted procedures for formulating pharmaceutical mixtures. Generally, the ingredients can be mixed in a mixer, blender, or other standard mixing device to produce a concentrated mixture. Sufficient time for mixing and procedures for elimination of lumps is used to ensure that a homogenous mixture is formed. Additional amounts of water can be added to obtain the desired concentration. The concentration of the buffering ingredients may also be adjusted to obtain the desired pH in the final composition. Alternatively, if the proper amounts of the various ingredients have been determined by prior experiments, these amounts can be added and mixed together in a mixing vessel without pH adjustment.

G. Administration of the Epileptic-seizure-inhibiting Composition

The composition of the present invention can be administered or applied to the rectum of a patient in anticipation of potential or imminent seizure or during the seizure period. While a single dose may be administered which is effective to inhibit the seizure, prophylactic doses can be given every eight hours to prevent the onset of seizures. Therefore, a single unit dose of about a 1 ml to about a 6 ml volume of the composition will be administered, which contains the necessary effective amount of the anti-epileptic agent.

The epileptic-seizure-inhibiting composition is preferably applied to the rectum by an applicator. Typically, the applicator is similar to a syringe. A preferred applicator has a cylindrical syringe barrel connected to an elongated, hollow delivery member that is adapted for insertion into the rectum of the individual to be treated. The elongated, hollow member may be about 4.4 cm to about 7 cm long, flexible, and equipped with a blunt, open tip. Preferably, the tip is blunt enough to obviate the risk of puncturing a patient's tissue when the elongated member of the applicator is inserted into the rectum, yet is small enough to facilitate easy insertion. It is also preferable that the elongated, hollow member be tapered for easy insertion into the rectum. Such an elongated, hollow member would facilitate the administration of the composition into the rectum without causing injury to the individual in seizure. The applicator further has a pressuring means associated with or operatively connected to the syringe barrel for forcing the epileptic-seizure-inhibiting composition out of the syringe barrel, through the elongated hollow member and into the rectum. For example, the pressuring means can be a plunger that can slide on the surface of the lumenal wall of the applicator.

Preferably, the applicator is made of a material that does not absorb or chemically react with the anti-epileptic agents in the epileptic-seizure-inhibiting composition. This is particularly important if the composition is stored in the applicator for an extended period of time. For example, the applicator can be made of plastic, such as rigid polypropylene or polyethylene. Glass and metal can also be used for making the applicator. However, if desired, part of the applicator can be constructed of a plastic material and another part with glass or metal. For example, a glass cartridge filled with a diazepam-containing composition can be inserted into an applicator having a plastic barrel. Because the glass cartridge is surrounded by the plastic barrel, the risk of glass breakage and injury to the patient is reduced.

Because of its relatively low cost, a plastic applicator has another advantage: it can be prepackaged with a single dose of the present composition as a disposable medicated applicator unit, for example, a medicated syringe-like assembly. In this case, the applicator may contain a suitable, premeasured volume of the composition for administration into the rectum. The loaded one-dose application functions as a single unit dosage form of the present composition. A prepackaged medicated applicator has an advantage of capable of providing for fast administration. A person only needs to open the package, remove from the end of the applicator any seal that is present, insert the tip member of the applicator in the rectum of the patient, and apply pressure to the barrel to deliver the epileptic-seizure-inhibiting composition into the rectum of the patient. It is also preferred to package a specific, premeasured amount of the composition in a cartridge-like container that is insertable into the applicator. The applicator is then used to deliver the composition from the cartridge to the rectum. In this case, the applicator may be reusable and the cartridge may be disposable. In this case, the loaded cartridge also represents a unit dosage form comprising the present composition. The volume of the composition prepackaged in the applicator can vary according to categories of body weight or whether the patient is a child or an adult.

A preferred embodiment of the invention is a kit comprising the syringe assembly preloaded with a premeasured dose of the present anti-epileptic agent as illustrated in the drawings. The syringe assembly is preferably contained in suitable packaging, such as a box, envelope or plastic blister pack, along with suitable instruction means for its use as described herein, such as a printed tag, label or package insert.

Referring to FIG. 1 and FIG. 2, the applicator 10 has a body 20. The body 20 has a cylindrical barrel 40 with a first end 41 and a second end 42, as well as a tapered, elongated, hollow member (or applicator tip) 30 connected to the first end 41 of a cylindrical barrel 40. A generally cylindrical cartridge 50 containing internally a premeasured volume of an epileptic-seizure-inhibiting composition (not shown) and a plunger 60 effective for forcing the composition out of the cartridge 50 can be inserted into the cylindrical barrel 40 through the second end 42 thereof. The elongated, hollow delivery member 30 has an axial internal passage 31 and tapers from the juncture between the elongated, hollow member 30 and the cylindrical barrel 40 to form a blunt open tip 35. At the juncture between the elongated, hollow member 30 and the cylindrical barrel 40 is a guard flange 43 to prevent the insertion of the cylindrical barrel 40 past the anus. The end 42 of the cylindrical barrel opposite the elongated, hollow member 30 is connected to two bridges 74, which are connected to finger grips 70, integral therewith, to be engaged by the fingers of the operator, during administration of the composition. Having two finger grips 70 instead of one continuous circular finger grip can provide better flexibility to enable snap-fitting of the flange 53 of cartridge 50 onto the end 42 of cylindrical barrel 40. The finger grips 70 are positioned perpendicular to the axis of the cylindrical barrel 40 and extend radially, each terminating in an inner ridge 73 facing the opening of the cylindrical barrel 40. The ridges 73, bridges 74, and the end of the cylindrical barrel 40 proximal to the bridges 74 define slots 75 for providing a snap-fit to accept and retain flanges 53 of the cartridge 50. The ridges 73 on the finger grips 70 each has an angled surface to facilitate the snap-fitting of the flange 53 of the cartridge 50. The ridges 73 are formed to a size to permit the cartridge 50 to be inserted into the cylindrical barrel 40 with ease, but prevent the cartridge 50 from being inadvertently removed from the barrel 40.

The cartridge 50 that can contain the epileptic-seizure-inhibiting composition has a hollow cylindrical body portion 55 connected on one end to a hollow neck portion 57 and connected on the other end to a flange 53. The outside diameter of the cartridge 50 is formed to a size to have a slip-fit into the barrel bore of the cylindrical barrel 40. The length of the cartridge 50 is of a size such that when the cartridge 50 is inserted into the cylindrical barrel 40, the neck portion 57 of the cartridge 50 extends slightly out of the cylindrical barrel 40 and into a tapered bore inside the elongated, hollow member 30. The plunger 60 has a relatively soft deformable piston head 63 and a plunger rod 64 attached to the piston head 63 at one end and to a flange 66 at another end. The piston head 63 can slide on the surface of the lumenal wall of the cartridge 50 near the end opposite the hollow neck portion 57.

The applicator 10, including the body 20, the cartridge 50 containing the epileptic-seizure-inhibiting composition, and the plunger 60, can be packaged as a unit. The neck portion 57 of the cartridge has an opening which can be covered with a releasable seal, such as a piece of plastic-aluminum-foil laminate to protect the composition in the cartridge 50. The opening at the other end of the cartridge can also be closed by a releasable seal, or can be closed by insertion of plunger head 63 partially into the cartridge. In use, the cartridge or cartridge-plunger assembly can be opened by removing the seal or seals from the cartridge 50. The cartridge 50 is then inserted into the cylindrical barrel 40 by snap-fitting the flange 53 of the cartridge 50 into the slots 75 defined by the ridges 73, bridges 74, and the end of the cylindrical barrel 40. The elongated, hollow member 30 of the applicator 10 is then inserted into the rectum of the patient. The epileptic-seizure-inhibiting composition is then administered to the patient by the operator manually engaging the finger grips 70 and the flange 66 of the plunger and by applying pressure on the plunger 60, thereby forcing the composition out of the cartridge 50 and the tip 35, and into the rectum of the patient.

Other embodiments of applicator may have flexible bulb-shaped bodies in which the epileptic-seizure-inhibiting composition of the present invention is stored. In use, the composition can be forced out of the bulb-shaped body into the rectum via the elongated, hollow member by squeezing the bulb-shaped body.

H. Characteristics of the Composition

While orally and intravenously administered epileptic-seizure-inhibiting compositions are not conveniently given to a patient in seizure with tonic spasm and clonic movement, the composition of the present invention is advantageously so employed. The composition of this invention is effective to inhibit epileptic seizure because it can be administered into the rectum in seconds and the anti-epileptic agent in the composition is absorbed quickly by the rectum.

The epileptic-seizure-inhibiting composition has a viscosity that is low enough that it can be inserted in seconds by using, for example, a syringe-like applicator. As a viscous substance, once inserted into the rectum, the composition can easily spread over a large surface area in the rectum. For this reason, the composition of the present invention has advantages over suppositories. Suppositories are slow to soften, and therefore, the time it takes for the anti-epileptic agent to be absorbed may be unreasonably long for the purpose of inhibiting seizure that is in progress. Clinical studies has shown that diazepam suppositories are inappropriate where a rapid effect is required (see Hughes et al., *Aust J. Hosp. Pharm.*, 14:2, 73–75 (1984)). The composition of the present invention, however, can provide much faster absorption of the anti-epileptic agent.

The consistency of the composition of the present invention is also viscous enough to substantially prevent leakage from the rectum. A patient in seizure often is in convulsion and frequently has no control over the rectal sphincter. Such a patient is not capable of voluntarily tightening the sphincter muscle to retain the liquid anti-epileptic drug inside the rectum. The convulsive movement exacerbates the problem of leakage of the liquid anti-epileptic agent. If an anti-epileptic agents is given rectally in liquid form, the seizure-inhibiting effect may not be realized because a low viscosity liquid has a tendency to leak out from the anus.

In intravenously administration of epileptic-seizure-inhibiting compositions, the pH of the epileptic-seizure-inhibiting composition is maintained at a range that is compatible with the intravenous route of administration. The pH for an intravenously administered composition is adjusted to such a narrow range so as not to significantly affect the pH of the body. Generally, the pH of such an intravenous composition is maintained at about 6.2 to 7. However, the optimal pH for stability of the anti-epileptic agent may be at a different range. For a composition that is administered rectally, a wider range of pH may be suitable because there is a less risk of adversely affecting the pH of the blood. As a result, the epileptic-seizure-inhibiting composition can have a longer shelf life than intravenous solutions.

To illustrate the specific elements of the invention, the following examples are given. These examples are for illustrative purpose only and not to be unduly considered as limitations of this invention.

EXAMPLE 1

Epileptic-seizure-inhibiting Composition

Propylene glycol USP (10.6 kg), ethyl alcohol (2.65 kg), and benzyl alcohol (0.398 kg) were added to a clean stainless steel mixing vessel and mixed at 730 rpm at 25° C., and then benzoic acid USP (0.305 kg) was added into the mixture through a 20 mesh screen and mixed for ten minutes. Diazepam, USP (0.128 kg), was added into the mixture and mixed for an additional 20 minutes. Hydroxypropylmethyl cellulose, METHOCEL™ E50 LVP (1.113 kg) obtained from Dow Chemical Co., Midland, Mich. was added.

In a separate vessel, sodium benzoate, NF (1.02 kg) was mixed with deionized water (10.286 kg) until the sodium benzoate was dissolved.

The resulting sodium benzoate solution was then added into the mixture in the mixing vessel and mixed for 50 minutes at 1640 rpm. The resulting composition can be used to fill a 1–5 ml cartridge of an applicator such as that shown in FIG. 1 and FIG. 2. The cartridge is then inserted into the applicator, tip end first. Product is prevented from leaking out of the nozzle by a membrane, pin or other device. This applicator is then packaged in a kit with instructions for use by the caregiver.

Alternately, the cartridge may be filled, sealed with a stopper on the barren end and cap on the tip end. The applicator is then packaged in a kit with the filled cartridge. The cartridge can be assembled into the applicator at the time of use by the caregiver by removing the tip cap and inserting the cartridge into the applicator. The device is then ready for administration.

EXAMPLE 2

Epileptic-seizure-inhibiting Composition

An epileptic-seizure-inhibiting composition is made using a procedure analogous to that of Example 1 except 1.0 kg of phenobarbital sodium, USP (Windthrop) is used instead of 0.128 kg of diazepam.

This composition can be used to inhibit, for example, grand mal seizure.

EXAMPLE 3

Epileptic-seizure-inhibiting Composition

An epileptic-seizure-inhibiting composition is made using a procedure analogous to that of Example 1 except 0.128 kg of phenytoin sodium, USP (Park-Davis) is used instead of 0.128 kg of diazepam.

This composition can be used to inhibit, for example, grand mal seizure.

EXAMPLE 4

Bioavailability Study

A comparative, randomized single-dose 2-way crossover bioavailability with the diazepam viscous solution of Example 1 and Roche diazepam (valium®) injectable solution was conducted using as subjects 18 healthy adult males, age 18–45 years. A dosage of 15 mg of the composition of Example 1 was administered rectally and Roche valium® was administered intravenously by injection.

The results showed that the absolute bioavailability for the present rectal solution was 90.4% relative to the Roche injectable solution. Half-lives were similar and the maximum serum concentrations of diazepam (447 ng/ml for the present composition and 584 ng/ml for the Roche injectable) were both above the effective therapeutic concentration of approximately 200 ng/ml. The rectally administered dose is rapidly absorbed but the maximum concentration absorbed is lower than the injectable dose, lessening concern for adverse effects, such as respiratory arrest.

EXAMPLE 5

Use of the Epileptic-seizure-inhibiting Composition

When a adult patient is observed to have an epileptic seizure attack, the kit of Example 1 is opened and the applicator assembled by opening the sealed end of the cartridge and inserting the cartridge into the cylindrical barrel of the applicator, open end first, with the plunger extending out of the end of the barrel distal to the elongated, hollow member. The elongated, hollow member of the applicator is inserted past the anus into the rectum of the patient. Then the composition in the cartridge is then delivered into the rectum, within a span of about 2 seconds, by applying pressure on the plunger to force the composition past the open end of the cartridge and through the elongated, hollow member. After the composition has been delivered into the rectum, the elongated, hollow member is withdrawn from the rectum of the patient.

The present invention has been described in the foregoing specification. It is to be understood that modifications and alterations of the invention can be made without departing from the spirit and scope of the invention. The embodiments are presented for illustrative purposes only, and are not to be interpreted as limiting the scope of the invention.

What is claimed is:

1. A viscous, epileptic-seizure-inhibiting composition comprising:
    (a) about 0.1–2.5 wt-% of the total composition of an anti-epileptic agent;
    (b) a buffer system in an amount effective to maintain the pH of the composition at about 5.5–7.5;
    (c) about 1–10 wt-% of a cellulose ether thickener to impart a viscosity to the composition so that it is suitable for administration by rectal injection to a human patient; and
    (d) about 25–95 wt-% solvent.

2. The composition of claim 1 wherein the anti-epileptic agent is selected from the group consisting of barbiturates, benzodiazepines, dipropylacetic acid derivatives, hydantoins, oxazolidinediones and succinimides.

3. The composition of claim 2 wherein the anti-epileptic agent is diazepam.

4. The composition of claim 1 wherein the amount of the cellulose ether thickener is effective to impart an apparent viscosity of about 1,000 to about 8,000 cps to the composition.

5. The composition of claim 1 wherein the cellulose ether thickener is selected from the group consisting of methyl cellulose, carboxylmethylcellulose, hydroxypropylcellulose, and hydroxypropylmethylcellulose.

6. The composition of claim 5 wherein the cellulose ether thickener is hydroxypropyl methylcellulose.

7. The composition of claim 1 wherein the solvent is water or water and a water-miscible organic solvent in an amount effective to inhibit precipitation of the anti-epileptic agent from the composition.

8. A viscous, epileptic-seizure-inhibiting composition comprising:
    (a) about 0.25–0.75 wt-% diazepam;
    (b) a buffer system in an amount effective to maintain the pH of the composition at about 5.5–7.5;
    (c) about 1–10 wt-% cellulose ether thickener;
    (d) about 25–75 wt-% of a non-toxic water-miscible organic solvent; and
    (e) the balance, water.

* * * * *